United States Patent [19]

Gordon

[11] Patent Number: 4,657,345
[45] Date of Patent: Apr. 14, 1987

[54] LASER SHIELD AND METHOD OF MAKING SAME

[75] Inventor: Bruce S. Gordon, Shelton, Conn.

[73] Assignee: Barnes Engineering Company, Stamford, Conn.

[21] Appl. No.: 710,148

[22] Filed: Mar. 11, 1985

[51] Int. Cl.⁴ .............................................. G02B 5/22
[52] U.S. Cl. .................................... 350/311; 252/582
[58] Field of Search ............... 350/311; 252/582, 583; 250/515.1

[56] References Cited

U.S. PATENT DOCUMENTS

| | | | |
|---|---|---|---|
| 2,793,964 | 5/1957 | Gilbert et al. | 350/311 |
| 3,454,715 | 7/1969 | Larach et al. | 252/582 |
| 3,675,990 | 7/1972 | Kogelnik et al. | 350/311 |
| 3,687,863 | 8/1972 | Wacher | 252/582 |
| 4,114,985 | 9/1978 | Friedman | 250/515.1 |
| 4,268,413 | 5/1981 | Dabisch | 252/583 |
| 4,396,643 | 8/1983 | Kuehn et al. | 250/515.1 |

*Primary Examiner*—John K. Corbin
*Assistant Examiner*—Loha Ben
*Attorney, Agent, or Firm*—Parmelee, Bollinger & Bramblett

[57] ABSTRACT

A laser shield which absorbs narrow band radiation of a laser beam while transmitting broad band radiation encompassing the narrow band is provided by diffusing a layer of a chromophore selected from one or more porphyrin complexes which have been modified by metals forming a metallo-porphyrin complex. The chromophore or chromophores are combined with a solvent which are mixed for dissolving the chromophores in the solvent to provide a dissolved chromophore solution. A transparent matrix material is dipped or otherwise brought into contact with the solution for a predetermined time period at a predetermined temperature for diffusing the chromophore into the surface of the matrix material which has been softened by the solvent at the elevated temperature to thereby provide a layer of diffused chromophore which absorbs radiation in a narrow band corresponding to the characteristics of the chromophore while passing a substantial portion of all radiation applied thereto. The strain introduced into the softened surface is then removed by a heat annealing process which also increases the effective concentration of the chromophore by increasing its solubility in the matrix.

10 Claims, 1 Drawing Figure

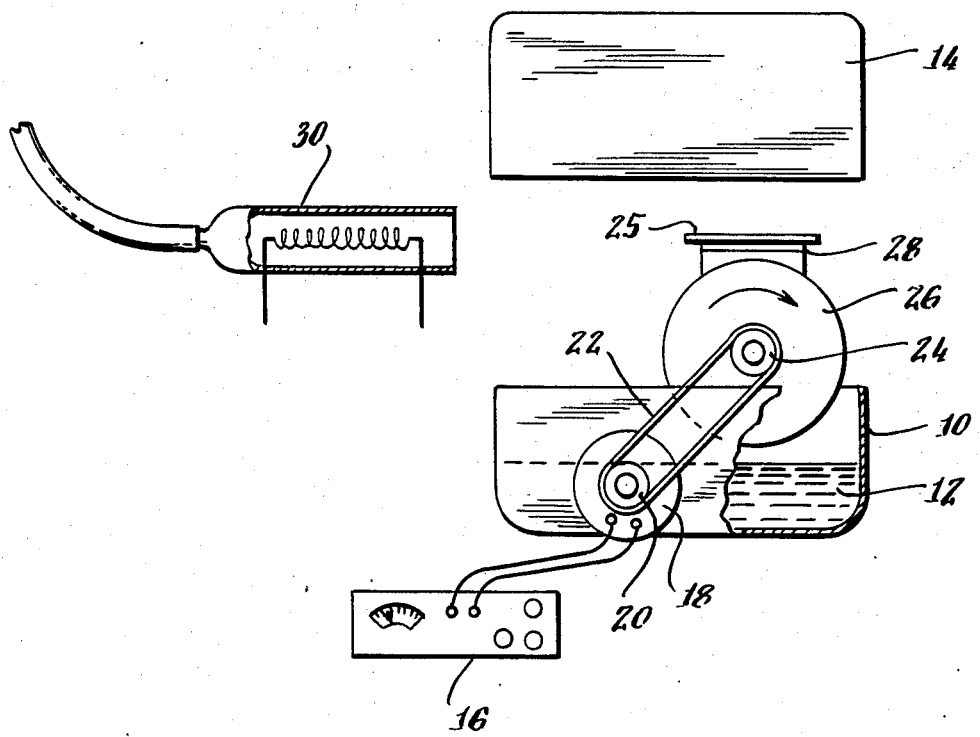

LASER SHIELD AND METHOD OF MAKING SAME

BACKGROUND OF THE INVENTION

This invention relates to a transparent protective laser shield and a method for making the same which is adapted to be interposed between a laser and a viewer for protecting the viewer from damage by laser beam radiation, and more particularly to such a protective shield in which chromophore dyes in the form of metallo-porphyrin complexes are diffused into the surface of a transparent host material, such as a plastic material, forming a diffused layer thereon thereby providing the host material with the absorption characteristics desired.

In a host of medical, industrial and other applications a laser beam may be employed for cutting, fusing or performing other functions which may cause contact with the eye either by direct viewing or reflection from the object being worked on. Since the eye collects and focuses the energy, and since the laser beam is generally concentrated, considerable damage can result from the application of this energy to the optic nerve. The same is true when the viewer happens to be a light sensitive detector which may be monitoring the particular operation being performed by the laser. Accordingly, laser shields have been provided to enable viewing the laser beam in its environment without being subjected to the danger of concentrated beam energy. For example, U.S. Pat. No. 3,853,783 describes the use of vanadyl phthalocyanine sulfonamides in plastic compositions to protect the eyes from exposure to laser radiation with wave lengths in the region of about 620 to 720 nanometers. The problem is to get the dyes, namely the vanadyl phthalocyanines to be readily soluble in the various transparent plastics which are used for the shields. In this patent the dyes are directly mixed with the plastic material and molded or cast into plates or goggles or shields, etc. which requires difficult and time consuming procedures and extreme difficulty in being able to thoroughly mix or dissolve the dyes in the plastic material.

SUMMARY OF THE INVENTION

Accordingly, it is an object of this invention to provide a transparent optical protective laser shield which absorbs optical radiation in a selected narrow band or band widths and transmits a broad band of optical radiation which includes and/or surrounds the absorbed narrow band wave lengths matching the laser beam desired to be protected against by diffusing the dyes into the host plastic material forming the laser shield.

A further object of this invention is to provide a new and improved laser shield and method of making the same which is simpler, increases the solubility of the dyes in the matrix and avoids trying to make the dye readily soluble in various transparent plastics.

In carrying out this invention in an illustrative embodiment thereof, a protective laser shield which absorbs narrow band radiation corresponding to a laser beam while transmitting broad band radiation is provided by combining at least one chromophore selected from one or more porphyrin complexes which have been modified by metals forming metalloporphyrin complexes with a solvent capable of thoroughly dissolving the added porphyrin complexes or dyes. The dyes and solvent are mixed for dissolving the chromophore in the solvent to provide a dissolved chromophore solution. The surface of a transparent matrix material is subjected to the dissolved chromophore solution by bringing the surface of the transparent matrix material into contact with the dissolved chromophore solution at predetermined temperatures for a predetermined period thereby diffusing a layer of the chromophores into the surface of the transparent matrix. A water vapor free environment is provided for the diffusion process to prevent the formation of water vapor on the transparent matrix material while the solvent evaporates and the surface cools when the matrix material is withdrawn from contact with the dissolved chromophore solution. The withdrawn matrix is then heat annealled which in effect increases the concentration of chromophore in the cured diffused surface.

Advantageously, the diffusion of the chromophores into a surface thereby forming a layer of the chromophores in the surface of the host or transparent plastic matrix material eliminates the previous requirement cited in the aforesaid patent for totally mixing or trying to dissolve the chromophore throughout the host material as well as any rearrangement or concentration of the chromophores in such material when it is cast since in accordance with the present laser shield, the chromophores or dyes are not cast or molded into the matrix material, but are simply diffused in an already formed shield.

BRIEF DESCRIPTION OF THE DRAWING

The invention together with further aspects, objects, features and advantages thereof will be more clearly understood from the following description taken in conjunction with the accompanying drawing which illustrates one form of apparatus which may be utilized to form the laser shield in accordance with the present invention.

DESCRIPTION OF THE PREFERRED EMBODIMENTS

The transparent protective laser shield and method of making the same may be in the form of a shield, plate, visor, window, goggles etc. which are adapted to prevent injury to the viewer from exposure to a laser beam having concentrated narrow band radiation which is adapted to be absorbed by the protective laser shield when the laser beam is viewed with the shield interposed between it and the viewer. In accordance with the present invention, the formation of the laser shield involves the diffusion of one material more particularly, a chromophore into the surface of another namely, the host or matrix material in the form of a transparent plastic. The diffusion is achieved by using a solvent to "open" or loosen the surface of the host material thereby allowing chromophore or dye to diffuse into it forming a layer thereon which permits the host material to absorb the radiation applied thereto corresponding to the absorption characteristics with the dye which has been diffused therein. The chromophores or dyes referred to are generally a functional group of chemical compounds that give rise to a color in a molecule and with the assistance of an auxochrome such as a hyperoxl or amino group produces a dye. In the past such dyes have been used for coloring in textiles and/for the same purpose when introduced into crystals, glasses, plastics or polycrystalline materials. The aforesaid patent illustrates the use of one specific compound in a transparent material in which the dye is dissolved into the material, and then cast or formed into a shield to absorb rather broad wave lengths. The present invention differs by diffusing a layer of dye into the surface of a host material as contrasted with mixing the chromophore with the host material and casting it into the shield as is done in the aforesaid patent, or in applying a coating by painting or otherwise placing a layer of the dye on the outer surface of the host material.

The first step in forming the laser shield in accordance with the present invention involves combining a dye into a suitable solvent. Dye is characterized as comprising a chromophore or chromophores selected from one or more porphyrin complexes which have been modified by metals for forming a metallo-porphyrin complex which is designed to absorb radiation in a specific narrow band or bands of wavelengths which match the wavelengths of the laser beam or beams which are desired to be protected against. Examples of such suitable chromophores are t-butylated vanadyl phthalocyanine/ and stanous chloride t-butylated phthalocyanine which absorb at 694 nanometers and are suitable for protection against a ruby laser; the platinum porphyrin of octaethylene porphyrin which is suitable for absorbing the double yag laser at 532 nanometers, etc. One or more metallo-porphyrin chromophores or dyes may be combined for diffusing one or more dyes into the surface of the host material for selective absorption of one or more narrow wave lengths in a broader wave length band.

The solvent is characterized by being able to perform the dual function of thoroughly dissolving the dye which has been combined therewith as well as being capable of entering the surface of the host material to which it is applied. Any solvent capable of dissolving the dye or chromophore and penetrating or softening the surface of the plastic host material may be utilized for example, dichloromethane, dichlorobenzene, chloroform, etc. The combined solvent and chromophore are mixed for dissolving the chromophore in the solvent to provide a dissolved chromophore solution. A transparent host or matrix material which provide the laser shield may be in the form of a window, visor, shield or plate, lens, goggles, etc. The host material is preferably a transparent plastic material with broad band transmission characteristics such as clear acrylic formed from methylmethacrylate, polycarbonate, polyvinyl chloride, polyethylenes, polyesters, etc.

The entire transparent matrix material or a surface thereof is brought into contact with the dissolved chromophore solution at a predetermined temperature and held in such contact for a predetermined period of time for diffusing the chromophore into the surface of the matrix material providing a layer therein for absorbing the desired narrow band wave length in accordance with the characteristics of the dye which has been diffused into the surface of the matrix material. The shield, plate, goggle, etc. of the matrix material may be brought into contact with the dissolved chromophore solution which may be filtered prior to the contact step for eliminating undissolved particulants in the chromophore solution. The contact may be done manually or preferably mechanically in order to more accurately control the temperature and time cycle.

One method of providing bringing the matrix material into contact with the dissolved chromophore solution is illustrated in the drawing which includes a seamless container 10 for holding dissolved chromophore solution 12 which container is provided with a cover 14. A motor speed control 16 is coupled to a motor drive 18 for rotating a drive pulley 20. The drive pulley 20 operates a drive belt 22 for driving a power transport pulley 24 for rotating rotary drum 26 with pegs for accommodating flexible plastic parts having a plastic plate holder 28 adapted to carry and bring the laser shield matrix 25 in contact with the soluble chromophore solution 12 carried by the container 10. A nitrogen gas heater 30 is provided for the dipping apparatus shown in the drawing which is level with the plastic plate attachment 28 in order to apply dry heated nitrogen gas to the surface of the plate attachment 28 when a matrix material 25 mounted thereon is withdrawn from dipping in the solution 12 in order to provide a water vapor free atmosphere for the withdrawn plate 25 in order to eliminate water vapor when the solvent evaporates and the surface of the diffused plate cools. Alternatively, a dehumidifier might also be employed.

Prior to the dipping or contact step, the optical density of the dissolved chromophore solution can be checked and the concentration adjusted to the desired optical density(OD) by the addition of more dye or solvent. The immersing, dipping or contact step is preferably made at a temperature between 25° to 50° C. which limits are determined by the boiling point of the solvent and/or the melting point of the plastic whichever is lower. It is also desirable to control the dipping or immersing time to between 1 to 10 seconds with 5 seconds being the best dipping or immersing time in order to provide an even diffused layer of chromophore in the surface of the laser shield being treated. The time period, of course, will also depend on the type of dye, the solvents, the type of matrix material and the temperature involved in the diffusion process.

After using the solvent to "open" or loosen the surface of the host material thereby permitting the chromophores to diffuse into it, the strain introduced into the surface of the host material is removed by a heat annealing process whose effects may be tested as the annealing process takes place. The heat annealing process increases the effective concentration of one or more of the chromophore dyes by in effect increasing their solubility in the host matrix material. The heat annealing process is a slow deliberate process and will depend on the type of host material and the chromophores which are diffused therein. One schedule for the annealing process which has been found suitable for diffusing dyes into polycarbonate for specific examples which follow is as follows:

SCHEDULE A
CONTROL OF TEMPERATURE FOR ANNEALING
OF DIFFUSED POLYCARBONATE

| $T_{min.}$ ° C. | $T_{max.}$ ° C. | Time Spent at T | |
| --- | --- | --- | --- |
| | | Min. | Max. |
| 55 | 65 | 2 hrs. | 12 hrs. |
| 100 | 110 | 4 hrs. | 12 hrs. |
| 120 | 125 | 2 hrs. | 12 hrs. |
| 140 | 145 | 0.15 hrs. | 2 hrs. |
| Slow (3–18 hr.) | | temperature drop to room T | |

Note:
Time is allowed (3 to 10 min.) for oven to reach listed temperature.

Although various materials may be utilized in accordance with the present invention, two specific examples which have been found suitable in accordance with the present invention are as follows:

EXAMPLE 1

A porphyrin dye compound t-butylated vanadyl phthalocyanine (t-bu VO Pc) is fully dissolved into chloroform at the rate of 0.690 mg/ml, with 5.2 mg/ml of antioxidant. This mixture is then warmed in an oven to 37° C. A warm (37° C.) plate of polycarbonate is then dipped into this mixture for 5 seconds. This plate is then immediately placed into an oven at the same temperature. After 24 hours the optical density (OD) at the wavelength of interest is read (1.9 OD). The plate is then placed in an oven at 60° C. The temperature of this oven is then controlled according to Schedule A. The plate is then tested for OD (OD=2.0) and strain relief [polarized light or surface explosion with solvent (acetone)].

A protective coating may be applied.

EXAMPLE 2

2.70 mg/ml platinum octaethylporphyrin (Pt OEP) and 0.245 mg/ml t-bu VO Pc are dissolved into warm chloroform and a polycarbonate plate is diffused as in Example 1 above. After diffusion, the OD's are 3.7 (Pt OEP) and 1.4 (t-bu VO Pc). After annealing by Schedule A, the OD's rise to 3.8 (Pt OEP) and 2.0 (t-bu VO Pc). These pieces may then be processed as in Example 1.

This process involves the use of chromophores individually or in combination, with or without an ultraviolet absorber, and with or without antioxidants or other modifiers such as plasticizer hardeners, etc.

Accordingly, a new and improved laser shield is provided by diffusing a layer of dye into the surface of a transparent protective laser shield as contrasted to merely applying an outer coating or painting a dye on the outer surface of the shield or incorporating the dye throughout the shield before it is formed or cast. This provides a more reliable controllable laser shield which simplifies the process of forming such a shield allowing for more accurate and uniform laser shields to be repetitively so formed.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following equivalents and claims thereto.

What is claimed is:

1. A method of making a laser shield which absorbs narrow band radiation of a laser beam while transmitting broad band radiation comprising the steps of:
    combining at least one chromophore selected from one or more porphyrin complexes which may have been modified by metals forming a metallo-porphyrin complex with a solvent capable of dissolving the added porphyrin complexes,
    mixing the combined solvent and chromophore for dissolving the chromophore in said solvent to provide a dissolved chromophore solution,
    softening at least one surface of a transparent matrix material by bringing the surface of said transparent matrix material into contact with the dissolved chromophore solution at a predetermined temperature for a predetermined time period and thereby diffusing the chromophore in said solvent into said softened surface of said matrix material,
    heat annealing said transparent matrix material for increasing the effective concentration of chromophore diffused into said matrix material.

2. The method claimed in claim 1 including the step of filtering the dissolved chromophore solution to eliminate undissolved particulants.

3. The method claimed in claim 1 wherein the predetermined temperature employed in diffusing the chromophores into the surface of the matrix material is in the range of 25° C. to 50° C.

4. The method claimed in claim 1 wherein the predetermined time period for bringing the dissolved chromophore solution into contact with the surface of the matrix material is in the range of 1–10 seconds.

5. The method claimed in claim 1, wherein the predetermined temperature employed and the predetermined time period in the diffusion step are in the range of 25° C. to 50° C. and 1–10 seconds, respectively.

6. The method claimed in claim 1, including the step of providing a water free environment for said diffusion step to prevent the formation of water vapor on the diffused surface.

7. The method claimed in claim 6, in which the water vapor free environment is provided by applying heated dry nitrogen gas to the surface of the matrix material as such surface is removed from contact with the dissolved chromophore solution.

8. The method as claimed in claim 1, wherein the chromophore selected is t-butylated vanadyl phthalocyanine which is mixed with chloroform and is brought into contact with a polycarbonate plate having approximately the same temperature as the chloroform mixture.

9. The method as claimed in claim 1, wherein the chromophores selected are t-butylated vanadyl phthalocyanine and platinum octaethylporphyrin which are mixed with chloroform and brought into contact with a polycarbonate plate having approximately the same temperature as the polycarbonate plate.

10. A laser shield which absorbs predetermined narrow band radiation while transmitting broad band radiation comprising:
    a solid piece of transparent matrix material of plastic material selected from a plastic group comprising acrylic, polycarbonate, polyvinyl chloride, polyethylene, and polyester,
    at least one surface of said solid piece of transparent matrix material having a diffused layer of chromophore therein, said chromophore formed of a metallo-porphyrin complex which causes said matrix material to absorb predetermined narrow band radiation whereby preselected narrow band radiation is absorbed in accordance with the type of diffused chromophore while substantial transmission takes place through said matrix material in a broader band which encompasses said absorbed narrower band of radiation.

* * * * *